US012193956B2

(12) United States Patent
Koroschetz et al.

(10) Patent No.: US 12,193,956 B2
(45) Date of Patent: Jan. 14, 2025

(54) UROLOGICAL CHITOSAN STENT AND DELIVERY SYSTEM

(71) Applicant: OLYMPUS CORPORATION, Tokyo (JP)

(72) Inventors: Moritz Koroschetz, Boston, MA (US); Seiichi Ito, Lexington, MA (US)

(73) Assignee: Gyrus ACMI, Inc., Westborough, MA (US)

(*) Notice: Subject to any disclaimer, the term of this patent is extended or adjusted under 35 U.S.C. 154(b) by 1052 days.

(21) Appl. No.: 17/066,009

(22) Filed: Oct. 8, 2020

(65) Prior Publication Data
US 2021/0106730 A1 Apr. 15, 2021

Related U.S. Application Data

(60) Provisional application No. 62/912,691, filed on Oct. 9, 2019.

(51) Int. Cl.
*A61F 2/958* (2013.01)
*A61F 2/04* (2013.01)

(52) U.S. Cl.
CPC ........ *A61F 2/958* (2013.01); *A61F 2002/047* (2013.01); *A61F 2210/0004* (2013.01); (Continued)

(58) Field of Classification Search
CPC ...... A61F 2/82; A61F 2/94; A61F 2/95; A61F 2/9525; A61F 2002/821; A61F 2002/9583; A61F 2/04; A61F 2/07; A61F 2002/047; A61F 2210/0004; A61F 13/05; A61M 25/1011; A61M 2025/1052; A61M 2025/105; A61M 2025/1081; A61M 2210/166; A61M 2210/16;
(Continued)

(56) References Cited

U.S. PATENT DOCUMENTS 9,510,959 B2 * 12/2016 Shoham .................... A61F 2/91
9,517,122 B2 * 12/2016 Firstenberg ............. A61F 2/064
(Continued)

FOREIGN PATENT DOCUMENTS

CN 104042376 9/2014
CN 107334562 11/2017
(Continued)

OTHER PUBLICATIONS

"Chinese Application Serial No. 202010788273.2, Office Action mailed Oct. 10, 2023", W/O English Translation, 7 pgs.
(Continued)

*Primary Examiner* — Seema Mathew
(74) *Attorney, Agent, or Firm* — Schwegman Lundberg & Woessner, P.A.

(57) ABSTRACT

An apparatus includes a first layer, wherein the first layer comprises a scaffold structure forming an inner lumen along a length of the scaffold structure, and wherein the first layer comprises a bioresorbable material; a second layer on the first layer, wherein the second layer comprises a bioresorbable material configured to expand, wherein the second layer is positioned on the first layer such that ends of the first layer extend beyond ends of the second layer; and an expandable balloon located within a distal end of the inner lumen of the first layer.

21 Claims, 9 Drawing Sheets

(52) U.S. Cl.
CPC .............. *A61F 2210/0076* (2013.01); *A61F 2250/0039* (2013.01)

(58) Field of Classification Search
CPC ........ A61M 25/10184; A61M 25/1002; A61M 2210/1078; A61M 25/10; A61M 25/1018; A61M 31/00; A61B 17/0057; A61B 17/1204; A61B 2017/00274; A61B 2017/12004
See application file for complete search history.

(56) References Cited

U.S. PATENT DOCUMENTS

| | | | | |
|---|---|---|---|---|
| 10,064,626 | B2 * | 9/2018 | Celermajer | A61B 17/12136 |
| 10,828,184 | B1 * | 11/2020 | Schwartz | A61F 2/90 |
| 11,357,651 | B2 * | 6/2022 | Venkatraman | A61K 31/337 |
| 2001/0018585 | A1 * | 8/2001 | McGovern | A61B 18/1485 |
| | | | | 606/41 |
| 2002/0007206 | A1 * | 1/2002 | Bui | A61F 2/962 |
| | | | | 623/1.11 |
| 2002/0082556 | A1 * | 6/2002 | Cioanta | A61B 18/04 |
| | | | | 604/113 |
| 2002/0165521 | A1 * | 11/2002 | Cioanta | A61M 25/1011 |
| | | | | 604/113 |
| 2002/0173818 | A1 * | 11/2002 | Reever | A61F 2/04 |
| | | | | 606/198 |
| 2003/0153899 | A1 * | 8/2003 | Eshel | A61M 25/0662 |
| | | | | 604/102.03 |
| 2003/0199993 | A1 * | 10/2003 | Gellman | A61L 31/10 |
| | | | | 623/23.75 |
| 2004/0059389 | A1 * | 3/2004 | Chornenky | A61N 1/325 |
| | | | | 607/3 |
| 2004/0172112 | A1 * | 9/2004 | Cioanta | A61H 9/0078 |
| | | | | 607/113 |
| 2004/0193283 | A1 * | 9/2004 | Rioux | A61M 25/04 |
| | | | | 623/23.66 |
| 2004/0230188 | A1 * | 11/2004 | Cioanta | A61B 18/04 |
| | | | | 606/34 |
| 2004/0230316 | A1 * | 11/2004 | Cioanta | A61M 25/1011 |
| | | | | 623/1.21 |
| 2006/0009832 | A1 * | 1/2006 | Fisher | A61F 2/958 |
| | | | | 623/1.11 |
| 2006/0095124 | A1 * | 5/2006 | Benz | A61F 2/04 |
| | | | | 623/1.49 |
| 2007/0255394 | A1 * | 11/2007 | Ryan | A61F 2/2418 |
| | | | | 623/1.24 |
| 2008/0015671 | A1 * | 1/2008 | Bonhoeffer | A61F 2/2418 |
| | | | | 623/1.2 |
| 2009/0018533 | A1 * | 1/2009 | Perkins | A61B 18/1485 |
| | | | | 606/14 |
| 2009/0177288 | A1 * | 7/2009 | Wallsten | A61F 2/95 |
| | | | | 606/108 |
| 2010/0030263 | A1 * | 2/2010 | Cheng | A61B 17/0401 |
| | | | | 606/232 |
| 2010/0137978 | A1 * | 6/2010 | Atanasoska | A61L 31/088 |
| | | | | 427/2.24 |
| 2010/0145325 | A1 * | 6/2010 | Hoey | A61B 18/04 |
| | | | | 606/27 |
| 2010/0298948 | A1 * | 11/2010 | Hoey | A61B 18/04 |
| | | | | 606/27 |
| 2012/0089218 | A1 * | 4/2012 | Dardi | A61F 2/07 |
| | | | | 623/1.15 |
| 2014/0316509 | A1 | 10/2014 | Corrigan, Jr. | |
| 2018/0092732 | A1 * | 4/2018 | Kringle | A61F 2/04 |
| 2018/0344991 | A1 | 12/2018 | Cerchiari et al. | |
| 2021/0220178 | A1 * | 7/2021 | Avior | A61F 2/18 |

FOREIGN PATENT DOCUMENTS

| | | |
|---|---|---|
| CN | 112641544 | 9/2024 |
| JP | 2005511199 A | 4/2005 |
| JP | 2013223663 A | 10/2013 |
| JP | 7036518 B2 | 3/2022 |
| WO | 03049643 | 6/2003 |
| WO | WO-2012011261 A1 | 1/2012 |
| WO | WO-2017161331 A1 | 9/2017 |
| WO | 2019142077 | 7/2019 |

OTHER PUBLICATIONS

"Chinese Application Serial No. 202010788273.2, Response filed Feb. 2, 2024 to Office Action mailed Oct. 10, 2023", w english claims, 16 pgs.

"European Application Serial No. 20197288.2, Extended European Search Report mailed Mar. 9, 2021", 4 pgs.

"European Application Serial No. 20197288.2, Communication Pursuant to Article 94(3) EPC mailed Mar. 26, 2021", 6 pgs.

"Chinese Application Serial No. 202010788273.2, Voluntary Amendment filed Apr. 21, 2021", with English translation of claims, 14 pgs.

"European Application Serial No. 20197288.2, Response filed Jul. 23, 2021 to Communication Pursuant to Article 94(3) EPC mailed Mar. 26, 2021", 5 pgs.

"Japanese Application Serial No. 2020-151925, Notification of Reasons for Refusal mailed Jul. 13, 2021", w/ English Translation, 12 pgs.

"Japanese Application Serial No. 2020-151925, Response filed Sep. 13, 2021 to Notification of Reasons for Refusal mailed Jul. 13, 2021", with English translation of claims, 10 pgs.

"Chinese Application Serial No. 202010788273.2, Office Action mailed Apr. 3, 2024", w/ English Translation, 14 pgs.

"Chinese Application Serial No. 202010788273.2, Response filed May 30, 2024 to Office Action mailed Apr. 3, 2024", w/ current English claims, 15 pgs.

"European Application Serial No. 20197288.2, Communication Pursuant to Article 94(3) EPC mailed May 2, 2024", 6 pgs.

"European Application Serial No. 20197288.2, Response filed Aug. 27, 2024 to Communication Pursuant to Article 94(3) EPC mailed May 2, 2024", 9 pgs.

* cited by examiner

UROLOGICAL CHITOSAN STENT AND DELIVERY SYSTEM

CROSS-REFERENCE TO RELATED APPLICATION

This application claims the benefit of priority to U.S. Provisional Patent Application Ser. No. 62/912,691 filed on Oct. 9, 2019, the contents of which are incorporated herein by reference in their entirety

BACKGROUND

Field of the Invention

The exemplary and non-limiting embodiments described herein relate generally to surgical procedures. The exemplary and non-limiting embodiments described herein relate more particularly to apparatuses and methods of stent use in urological procedures.

BRIEF DESCRIPTION OF PRIOR DEVELOPMENTS

Various types of surgeries are used to treat urinary problems caused by an enlarged prostate. One such type of surgery is trans-urethral resection of the prostate (TURP), which involves the insertion of a stent into the urethra and the removal of excess prostate tissue that interferes with the flow of urine. The excess tissue is trimmed from the prostate using a resectoscope and is extracted through the stent.

After the surgical treatment of the prostate, the stent is removed and a 3-way catheter is placed into the patient's urethra for continuous bladder irrigation (CBI). In the case of CBI, patients may be kept overnight in an observation area. A solution used for the irrigation and flushing is collected and assessed for indications of complications resulting from the surgery. A patient is generally kept catheterized for 24 to 48 hours after any prostate surgery. When the collected solution provides an indication that there are no complications, the catheter is removed. Although some catheters (for example, 2-way catheters) can be left in the patient when the patient is released from the hospital, removal of a 3-way catheter is done before the patient is released.

Some configurations of prostatic chitosan stents used in urological procedures have a closed tip at the distal end that does not allow the insertion of the catheter past the braid and chitosan sponge of the stent to a suitable depth into the bladder. If the catheter is not inserted to a suitable depth, irrigation and flushing of the bladder may be insufficient. Other configurations have a more open tip, but the catheter is then required to be thin enough (for example, a 14 Fr. catheter) for inserting past the braid and chitosan sponge. Configurations of the latter type may also provide insufficient irrigation due to the thin size of the catheter.

SUMMARY

In accordance with one aspect of the invention, an apparatus comprises: a first layer, wherein the first layer comprises a scaffold structure forming an inner lumen along a length of the scaffold structure, and wherein the first layer comprises a bioresorbable material; a second layer on the first layer, wherein the second layer comprises a bioresorbable material configured to expand, wherein the second layer is positioned on the first layer such that ends of the first layer extend beyond ends of the second layer; and an expandable balloon located within a distal end of the inner lumen of the first layer.

In accordance with another aspect of the invention, an apparatus comprises: a scaffold structure forming an inner lumen along a length thereof, the scaffold structure being substantially tubular in shape and expandable in radial directions from an axis extending longitudinally through the tubular shape of the scaffold structure, an expandable layer on the scaffold structure and covering a portion of the scaffold structure along a length thereof such that a distal end of the scaffold structure extends beyond a distal end of the expandable layer and a proximal end of the scaffold structure extends beyond a proximal end of the expandable layer, wherein a material of the second layer is configured to expand, and an expandable balloon located within the distal end of the scaffold structure.

In accordance with another aspect of the invention, a method comprises: inserting an apparatus into a prostatic urethra of a patient, wherein the apparatus comprises a stent comprising a first layer comprising a scaffold structure of a bioresorbable material forming an inner lumen along a length of the scaffold structure, a second layer on the first layer, the second layer comprising a bioresorbable material configured to expand and being positioned on the first layer such that ends of the first layer extend beyond ends of the second layer, and an expandable balloon located within a distal end of the inner lumen of the first layer; expanding the balloon to position the stent in the prostatic urethra; expanding the second layer to cause the second member to press against an inner surface of the prostatic urethra; and collapsing the balloon and retracting the balloon through the inner lumen.

BRIEF DESCRIPTION OF THE DRAWINGS

The foregoing aspects and other features of the invention are explained in the following description, taken in connection with the accompanying drawings, wherein.

DETAILED DESCRIPTION

The example embodiments described herein are directed to urological stents and applicators and, more particularly to prostatic chitosan urological stents and associated applicators configured to be inserted into the urethra of a patient. In the example embodiments described, a combined stent and applicator has a catheter function, with the stent and the applicator being connected in series. This allows an inner lumen of the stent to remain sufficiently open to provide for both irrigation and drainage of an irrigation solution. In doing so, the need to insert a multi-lumen tube into the inner lumen of the stent is avoided. The applicator can be maintained in place with the prostatic chitosan stent to allow for irrigation of the bladder and drainage of the solution back through the applicator, thereby flushing the bladder.

Figure 1:
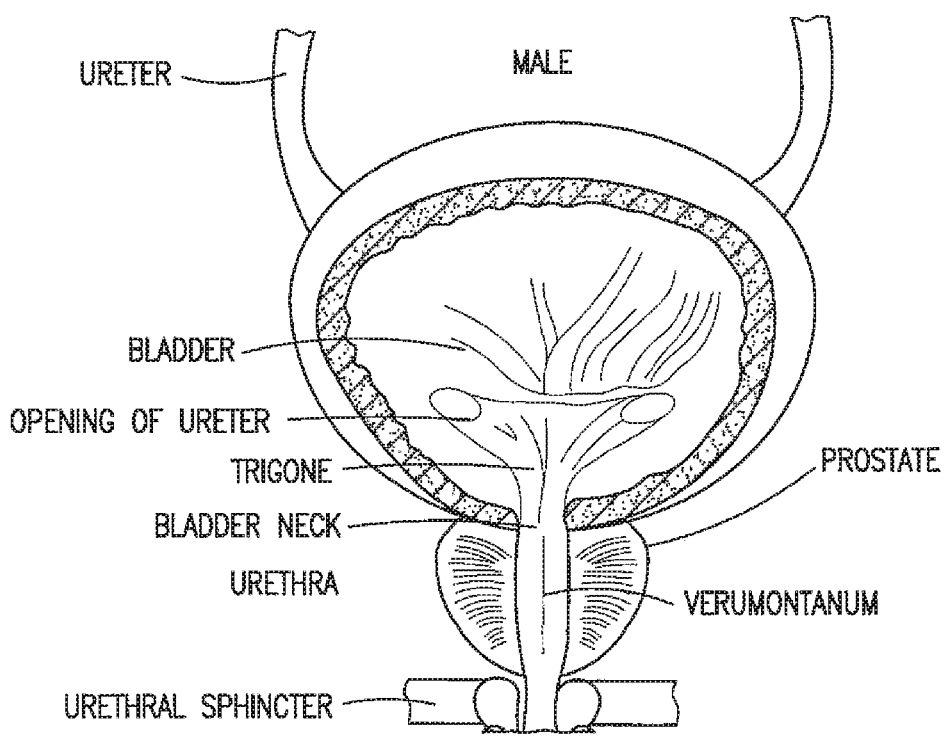
FIG. 1 is a diagram illustrating a portion of male human anatomy.

FIG. 1 is a diagram illustrating some features of male human anatomy. In particular, a bladder is shown along with various elements of the male urological system. The urethra extends from the bladder through the prostate and allows urine to pass. The locations of the urethral sphincter, which is a set of muscles that controls the flow of urine, the verumontanum, and the bladder neck are also shown.

Figure 2:
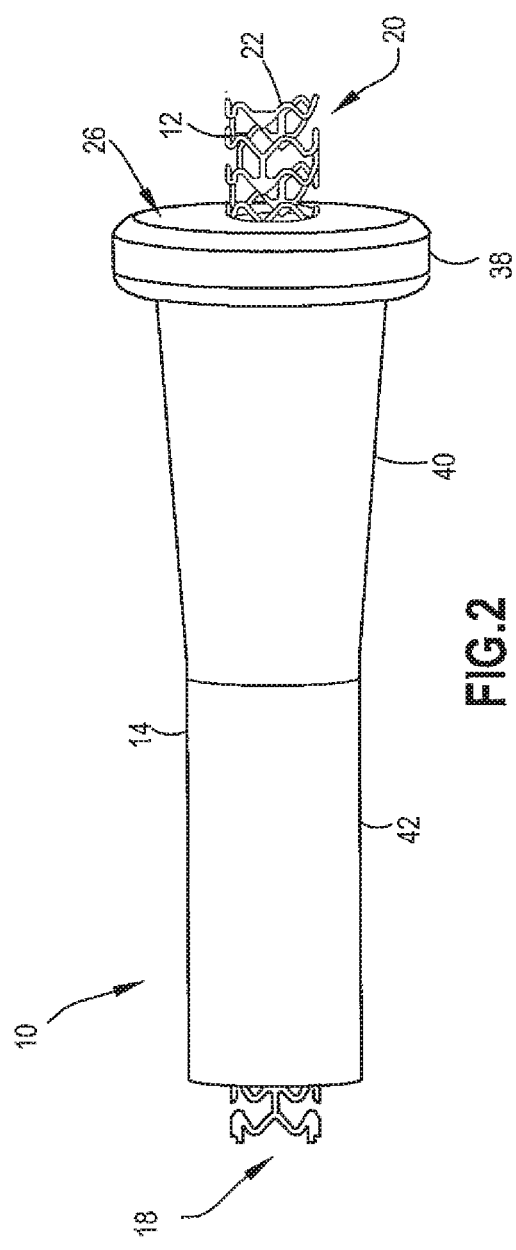
FIG. 2 is a side view of an example embodiment of a prostatic chitosan stent.
Figure 3:
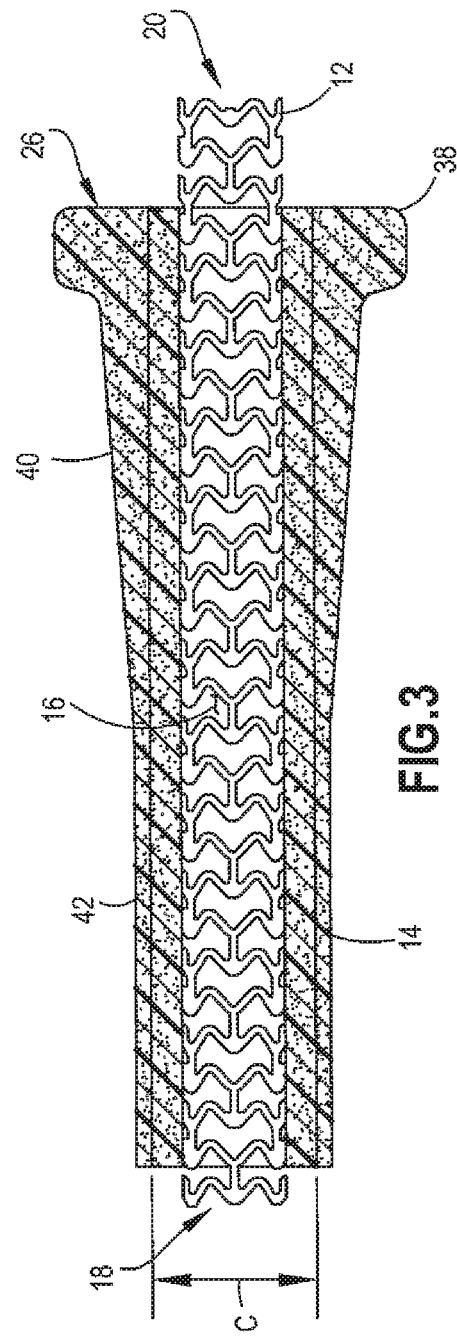
FIG. 3 is a side sectional view of the stent of FIG. 2.
Figure 4:
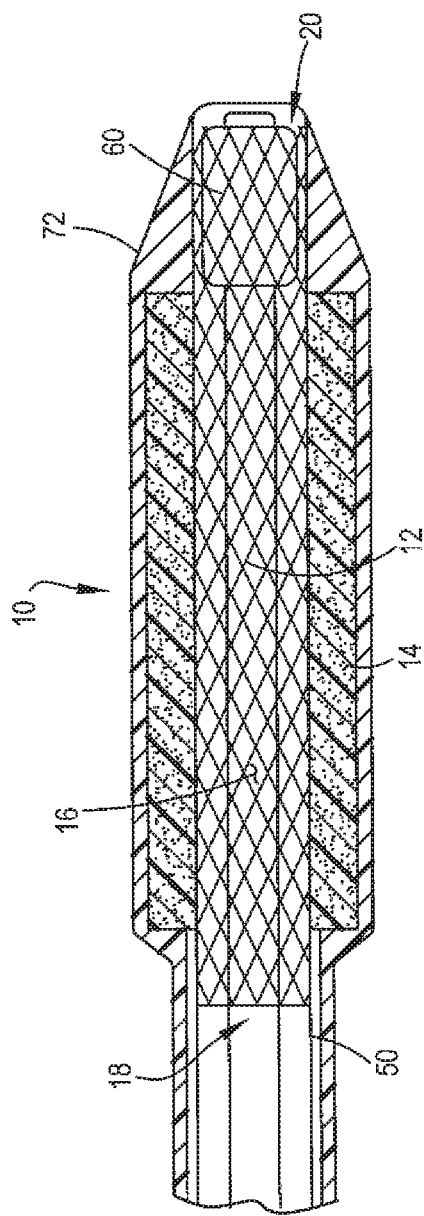
FIG. 4 is a schematic view of an example of a prostatic chitosan stent with an applicator.

Referring to FIGS. 2 and 3, one example of a prostatic chitosan stent is shown generally at 10 and is hereinafter referred to as "stent 10." In this example, the stent 10 comprises a first member 12 (braid) forming a first layer and a second member 14 (sponge layer) forming a second layer with the first member 12 retained in the second member 14. The second member 14 is either formed on the first member 12 or attached to the first member to form the stent as a unitary structure for insertion into the patient's urethra.

The first member 12 has a general tubular shape forming an inner lumen 16 between a proximal end 18 and a distal end 20. The first member 12 or braid, in this example, has a scaffold structure formed as a lattice or grille and comprises at least one bioresorbable material. In this example, the distal end 20 of the first member 12 has the lattice or grille forming an open tip 22 and extending outward from a distal end 26 of the second member 14. As shown in FIG. 3, the proximal end 18 of the first member 12 is also open and extends beyond the proximal end of the second member 14.

The second member 14 forms the layer around at least a portion of the scaffold structure of the first member 12. The second member 14 also comprises at least one bioresorbable material which may be at least partially the same as the bioresorbable material(s) of the first member 12.

The second member 14 has a substantially uniform outer diameter in the non-expanded configuration as shown by diameter C in FIG. 3, but expands into a non-uniform outer diameter as shown in FIGS. 2 and 3 as the second member 14 expands, such as by hydroscopic expanding or swelling for example, and/or by means of removing a compression covering. In this example, the non-uniform exterior shape of the second member 14 in its expanded configuration includes a distal section 38, a proximal section 42, and a middle section 40. The distal section 38 provides an enlarged section which is configured to be located inside the bladder and function as a bladder neck cover to seat against the bladder neck of the patient. This can help the user to position the stent 10 and prevent the stent 10 from moving away from the bladder neck, at least until dissolved. The middle section 40 can have a general conical shape extending down to the narrower diameter proximal section 42. The middle section 40 and the proximal section 42 can form the active length in the bladder. In one type of example, the shape of the middle section 40 and the proximal section 42 may be designed based upon clinical observations of the general shape of the area inside the prostate and usually formed by resection to thereby fit or fill the area efficiently. In this example, the second member 14 is formed as a chitosan sponge-type outer layer on the braid. A sponge-type outer layer allows for compression during a production process for easier insertion into the urethra of the patient.

Referring to FIGS. 4-8, one example of the prostatic chitosan stent 10 and a method of placing the stent 10 using an applicator 50 is shown. The generally tubular shape of the scaffold structure of the first member 12 is configured to provide structural strength and sufficient radial force to hold the urethra open and allow passage of urine through the inner lumen 16. The scaffold structure may be provided initially in a radially collapsed configuration about the longitudinal axis of the inner lumen 16, at least partially, which is subsequently allowed to expand or deploy, such as by self-expandable resilient deflection, into an expanded configuration.

Figure 5:
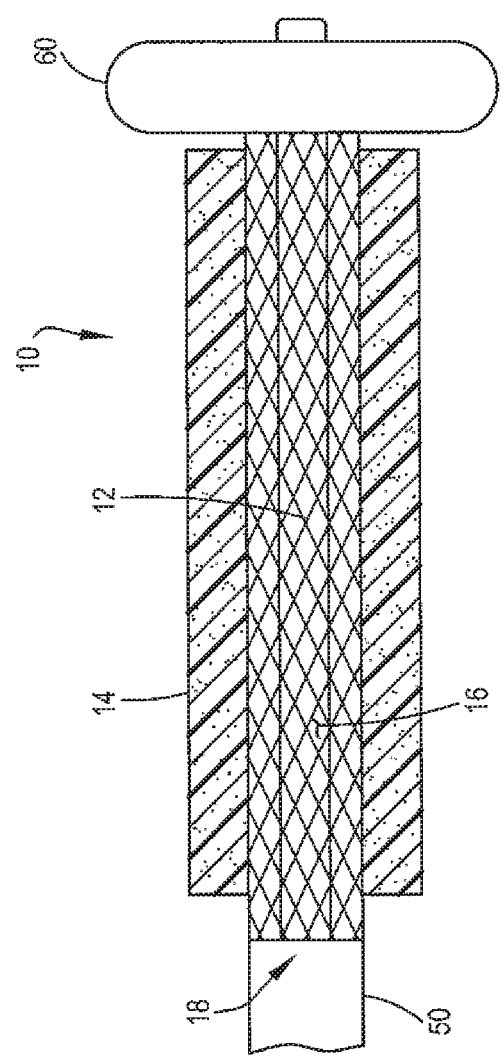
FIG. 5 is a schematic view of the stent and applicator of FIG. 4 illustrating an expanded balloon.

The stent 10 is serially located on a distal end of the applicator 50. The second member 14 is compressed and protected by the compression covering, which is a retractable protective film layer or cover and is hereinafter referred to as a sheath 72, which, as described below, is comprised of three layers. The stent 10 includes a balloon 60 that, in a non-expanded state (FIG. 4), is positioned in the distal end of the stent 10 within the first member 12. After the stent 10 is suitably located and at least a portion of the sheath 72 is removed, the balloon 60 may be expanded as shown in FIG. 5 to help position and hold the stent 10 relative to the prostate.

Figure 6:
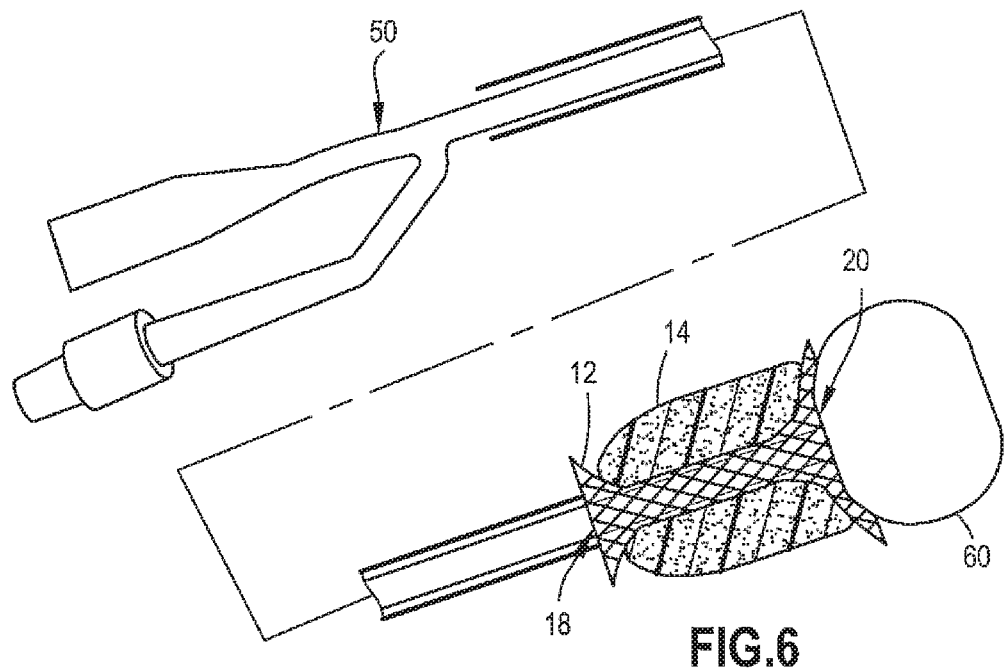
FIG. 6 is a schematic view of a prostatic chitosan stent in an expanded configuration with the balloon expanded.
Figure 7:
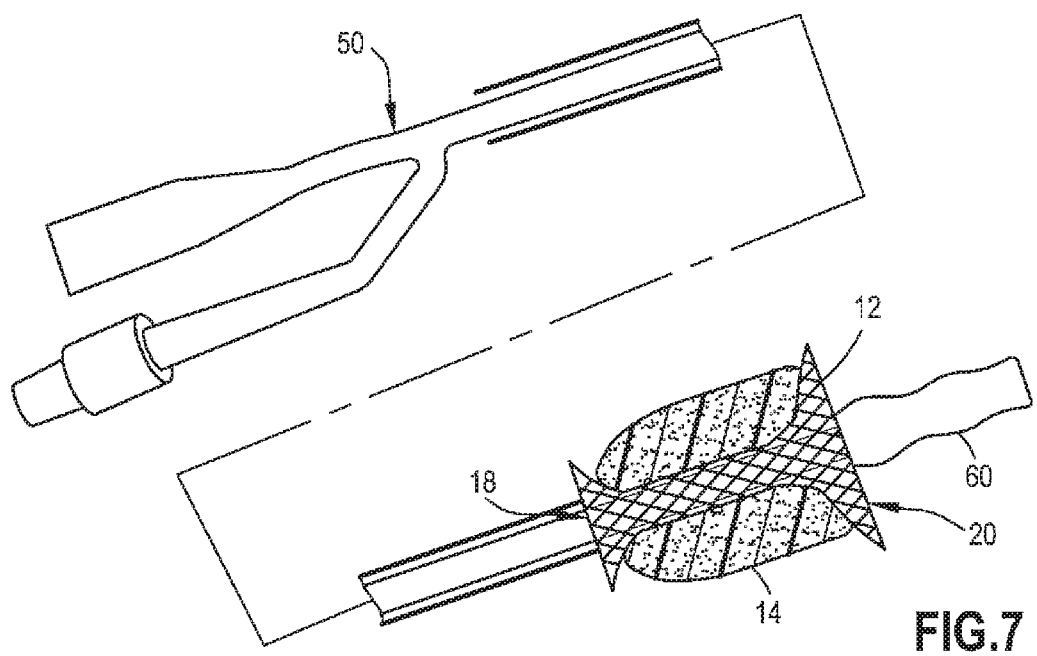
FIG. 7 is a schematic view of the stent of FIG. 6 with the balloon collapsed and prepared for retraction.

Referring now to FIGS. 6 and 7, because the first member 12 is longer than the second member 14 on both ends, both the proximal end 18 and the distal end 20 of the first member 12 (or braid) deform into funnel shapes when the first member 12 expands. The funnel shape at the distal end 20 allows the stent 10 to anchor between the verumontanum and the external urethral sphincter.

Still referring to FIGS. 6 and 7, the stent 10 is allowed to expand inside the patient. This expansion may be merely resilient expansion and/or hydroscopic expansion of the material of the second member 14 of the stent 10. If the expansion of the second member 14 is hydroscopic, such expansion may be due to contact with urine or other fluids.

Figure 8:
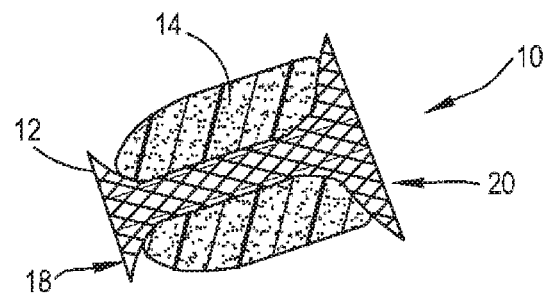
FIG. 8 is a schematic view of the stent of FIG. 7 with the balloon removed.

As shown in FIG. 7, the balloon 60 may be collapsed and retracted. Upon retraction of the balloon 60 and the applicator 50 from the proximal end 18 of the stent 10, the stent 10 remains deployed in the patient as shown in FIG. 8.

Figure 9A:
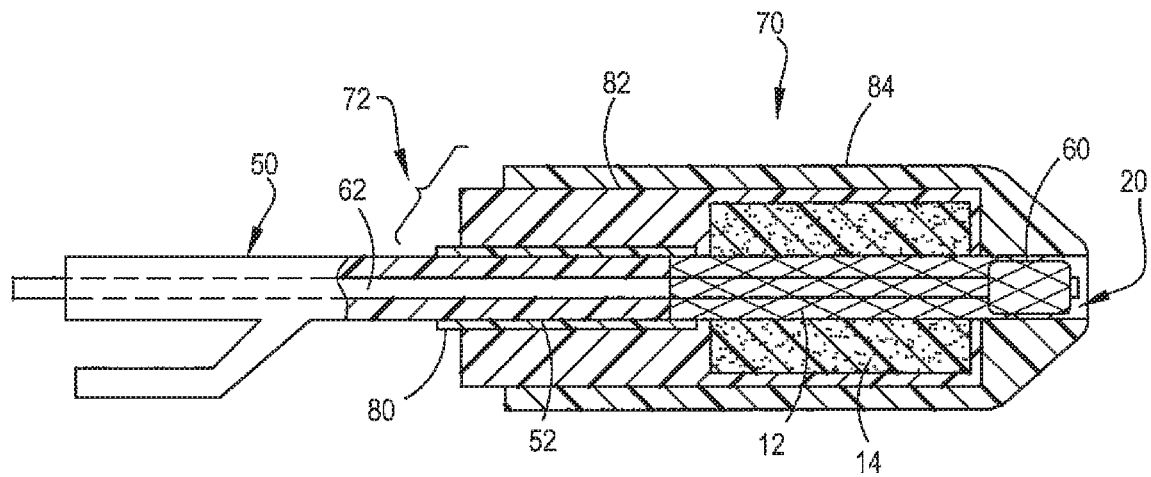
FIG. 9A is a schematic view of an example of a prostatic chitosan stent assembled with an applicator in preparation for deployment.
Figure 9B:
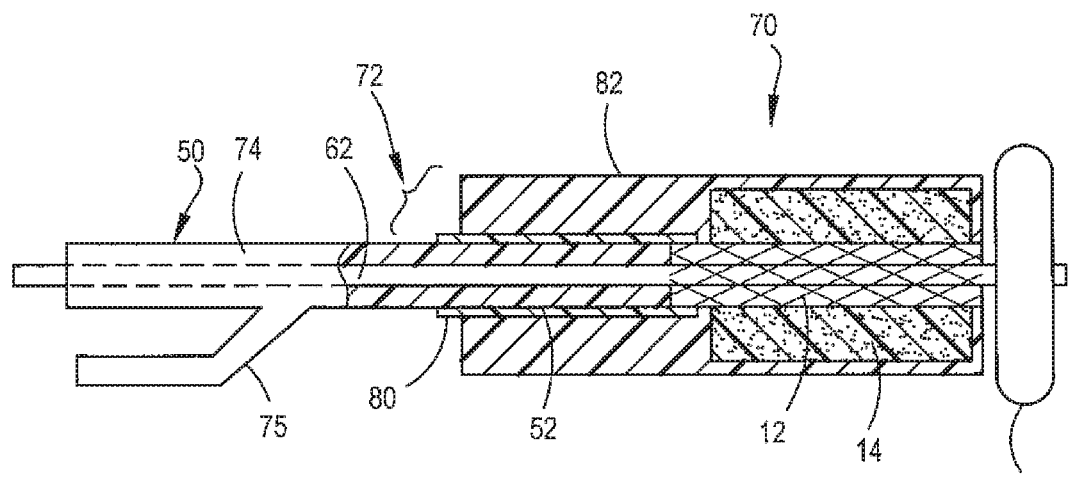
FIG. 9B is a schematic view of the stent of FIG. 9B with the balloon expanded.

Referring now to FIGS. 9A and 9B, an applicator/stent system is shown generally at 70 and is hereinafter referred to as "system 70." The system 70 comprises the applicator 50 having a main body 52 defined by a multi-lumen tube having a drain lumen 74 (first lumen) and an irrigation lumen 75 (second lumen), similar to that of a 2-way catheter, with the irrigation lumen 75 extending as the branched portion of the main body 52. The balloon 60 is operably coupled to a tube 62 and is expanded and retracted through the drain lumen 74 using the tube 62. The multi-lumen tube may also include a third lumen for additional functions. In any embodiment, the applicator 50 is serially coupled to the stent 10 defined by the first member 12 and the second member 14. As shown in FIG. 9A, the balloon 60 in non-expanded state is positioned at the distal end of and within the first member 12.

When the applicator 50 is serially coupled to the stent 10 to form the system 70, the sheath (shown at 72) having the three layers is located over a distal portion of the main body 52 and the stent 10. A first layer 80 (inner layer) of the sheath 72 covers the proximal end of the first member 12 and a portion of the main body 52 of the applicator 50 and couples the stent 10 to the main body 52 to maintain the catheter-like function of the system 70. In maintaining the catheter-like function, irrigation fluid may be delivered and drained through the applicator 50.

A second layer 82 (middle layer) of the sheath 72 covers from the distal end 26 of the second member 14 to the main body 52 to protect the second member 14 from contact with fluid.

A third layer 84 (outer layer) of the sheath 10 covers from the distal end of the stent 10 (with the balloon 60 therein) to the main body 52. The entire stent 10 assembled with the unexpanded balloon 60 is covered by the third layer 84. This third layer 84 may be stretchable to compress the applicator assembly to maintain the assembled stent 10, balloon 60, and applicator 50 sufficiently thin for insertion into a patient's urethra and to restrict the expansion of the stent 10.

After insertion of the assembled stent 10, balloon 60, and applicator 50 into the urethra of a patient, the third layer 84 (outer layer) is removed to expose the distal portion of the stent 10 with the balloon 60 therein. In doing so, the distal end 20 of the first member 12 and the balloon 60 are no longer restricted from being opened. As shown in FIG. 9B, the balloon 60 may be expanded, thus expanding the distal end 20 of the first member 12, to facilitate the positioning of the stent 10. Once the stent 10 is positioned, the second layer 82 (middle layer) is subsequently removed, thereby exposing the second member 14 to urine to allow the second member 14 to expand (in the case of hydroscopic expansion of the material of the second member 14). A suitable period of time (for example, about three minutes) is allowed to pass to ensure that the stent 10 is fully expanded. The balloon 60 may then be collapsed and retracted through the applicator 50. Once the balloon 60 is clear of the drain lumen 74, irrigation fluid may be delivered through the irrigation lumen 75 to the bladder.

Figure 10A:
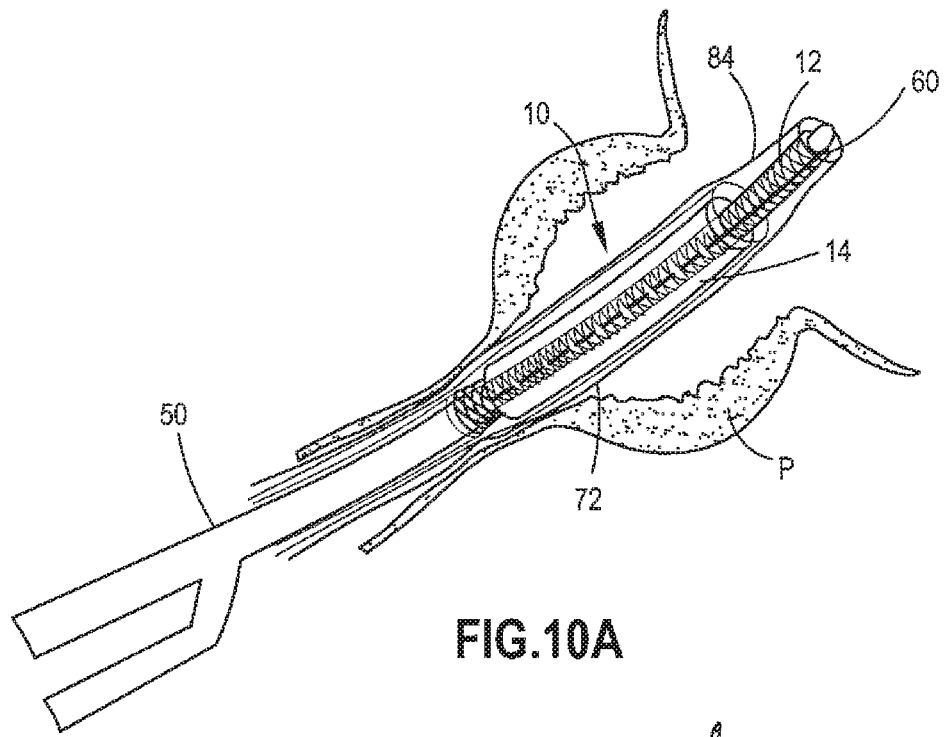
FIGS. 10A-10H are illustrations of a method of using an example prostatic chitosan stent.
Figure 10B:
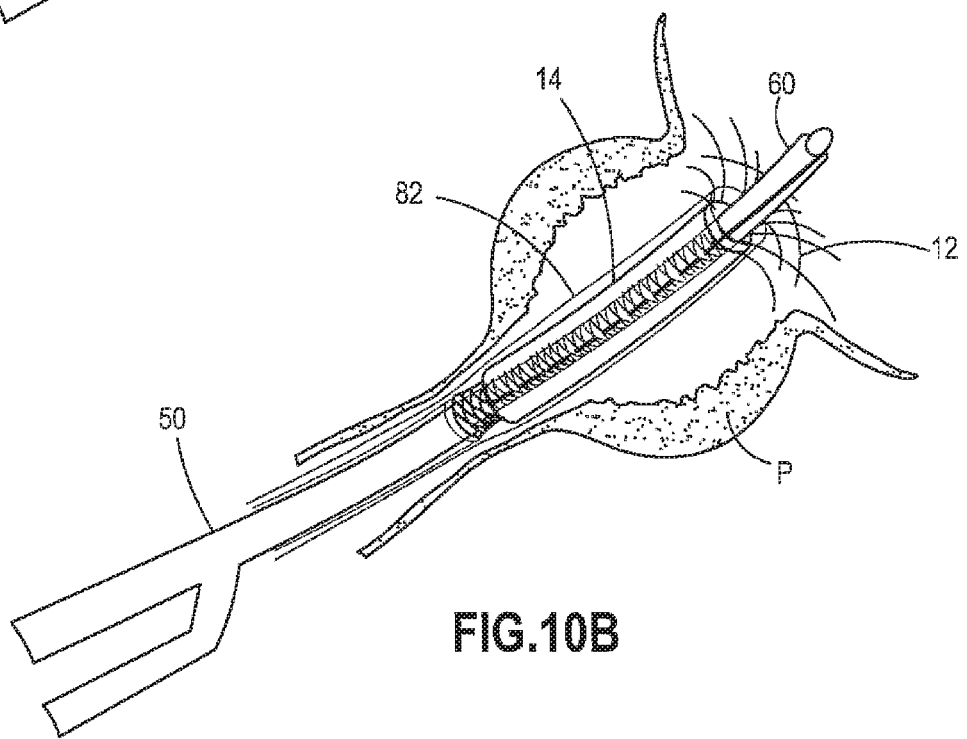
Figure 10C:
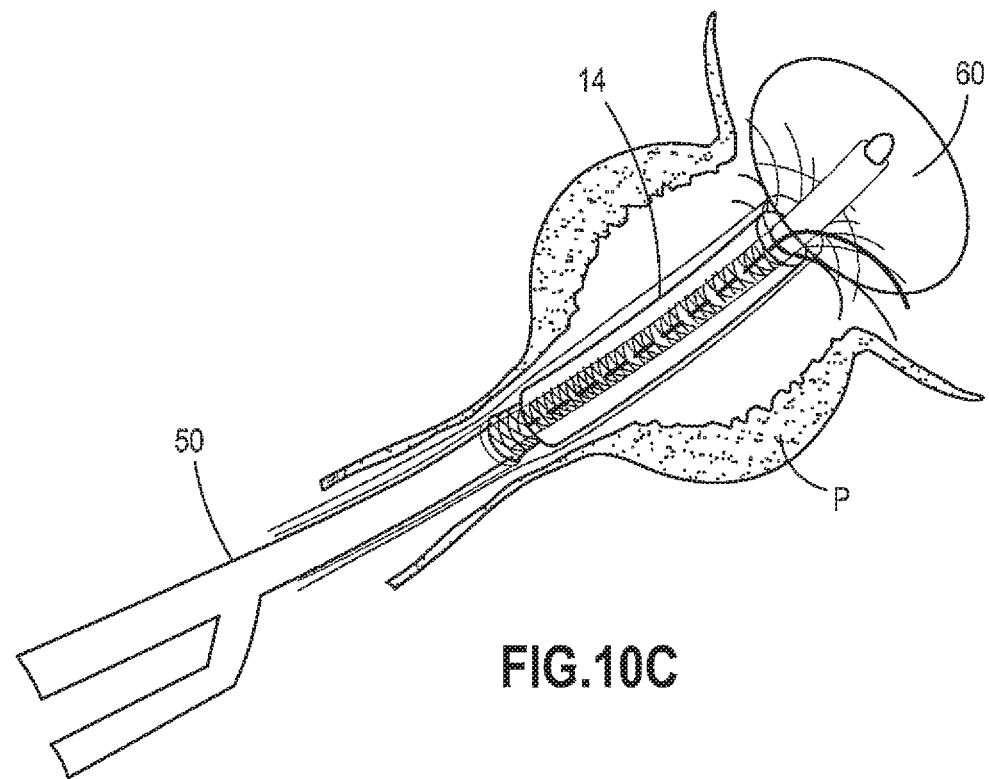
Figure 10D:
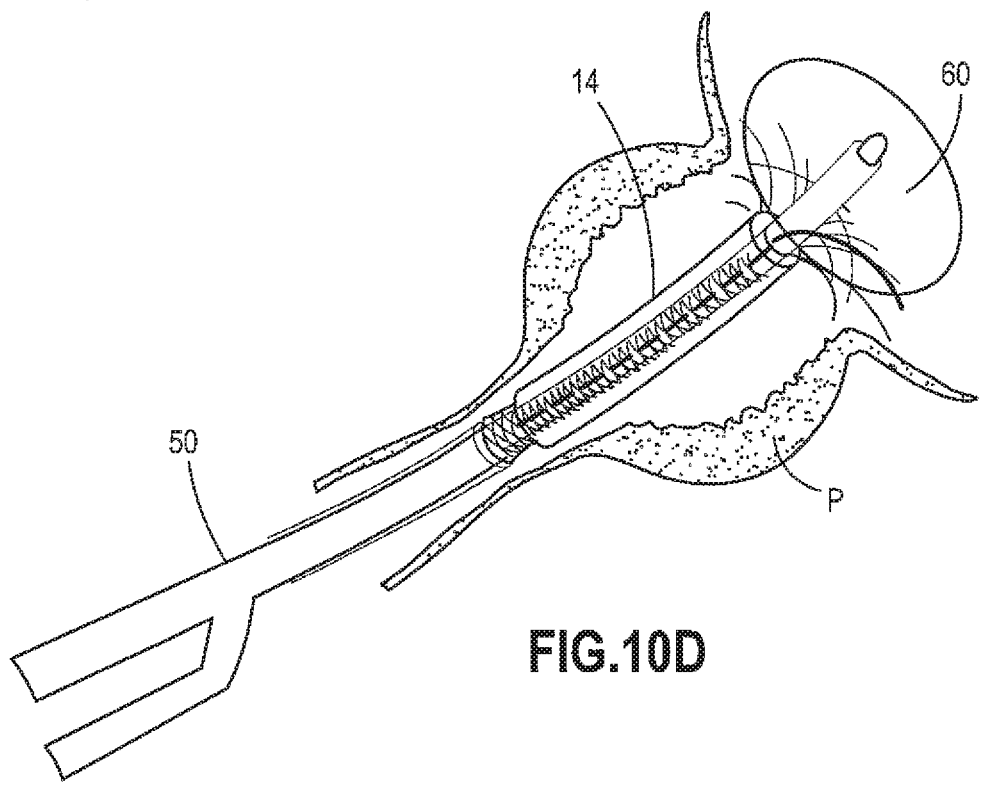
Figure 10E:
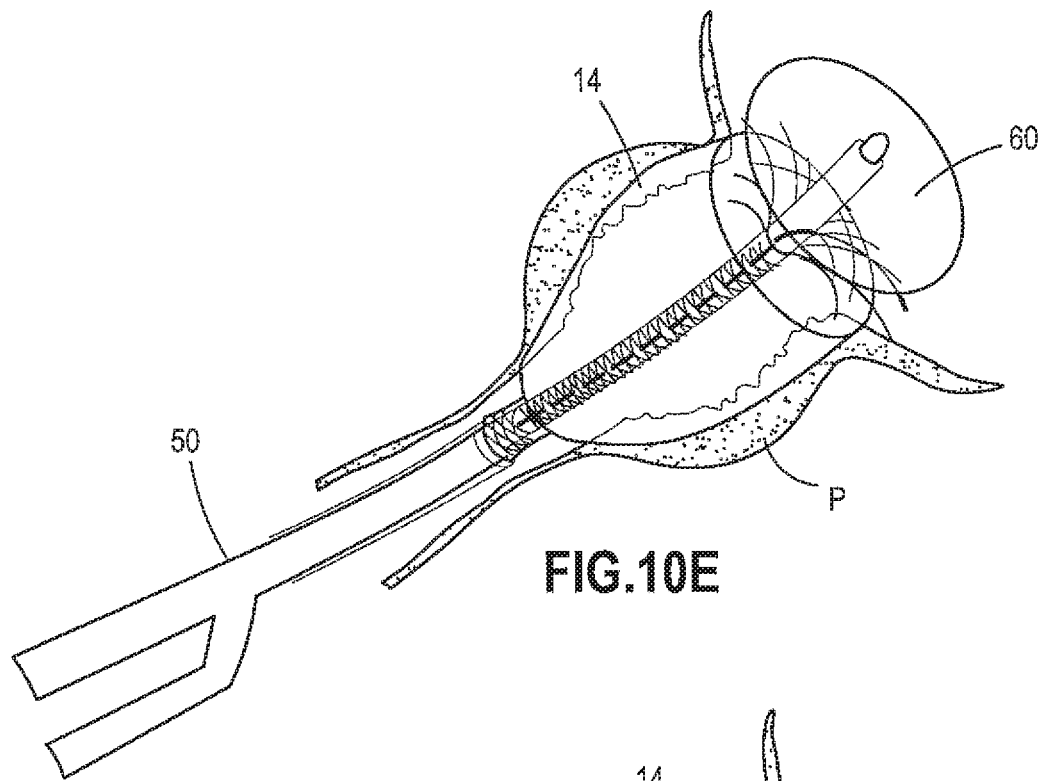
Figure 10F:
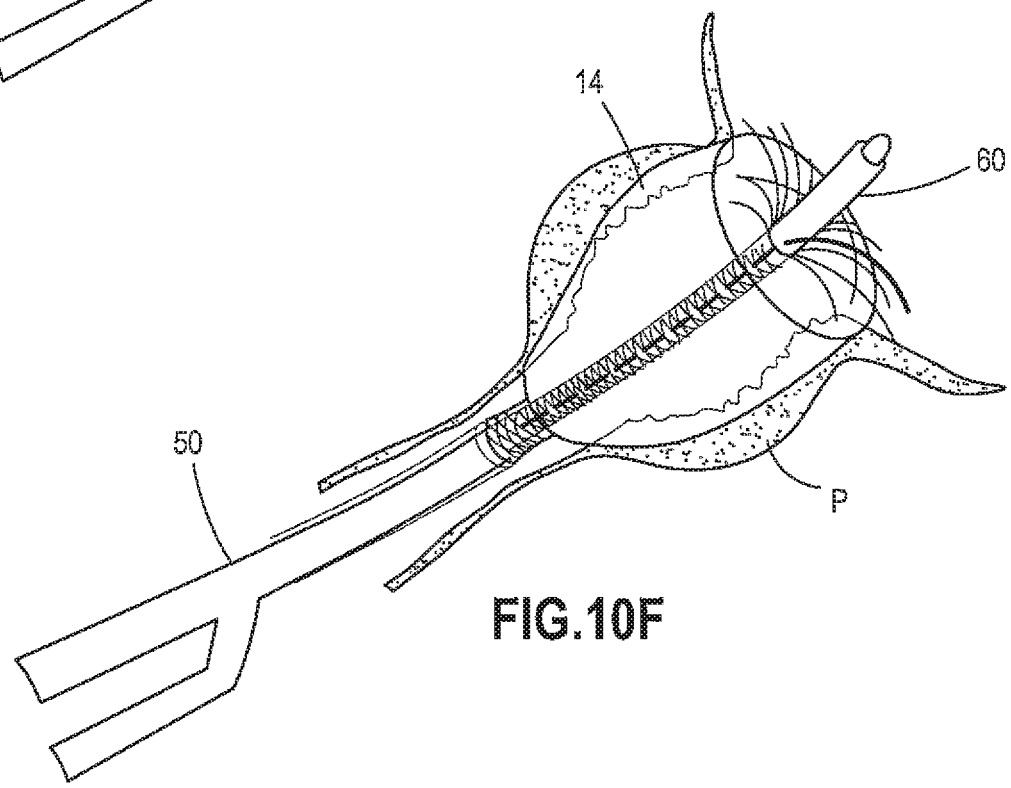
Figure 10G:
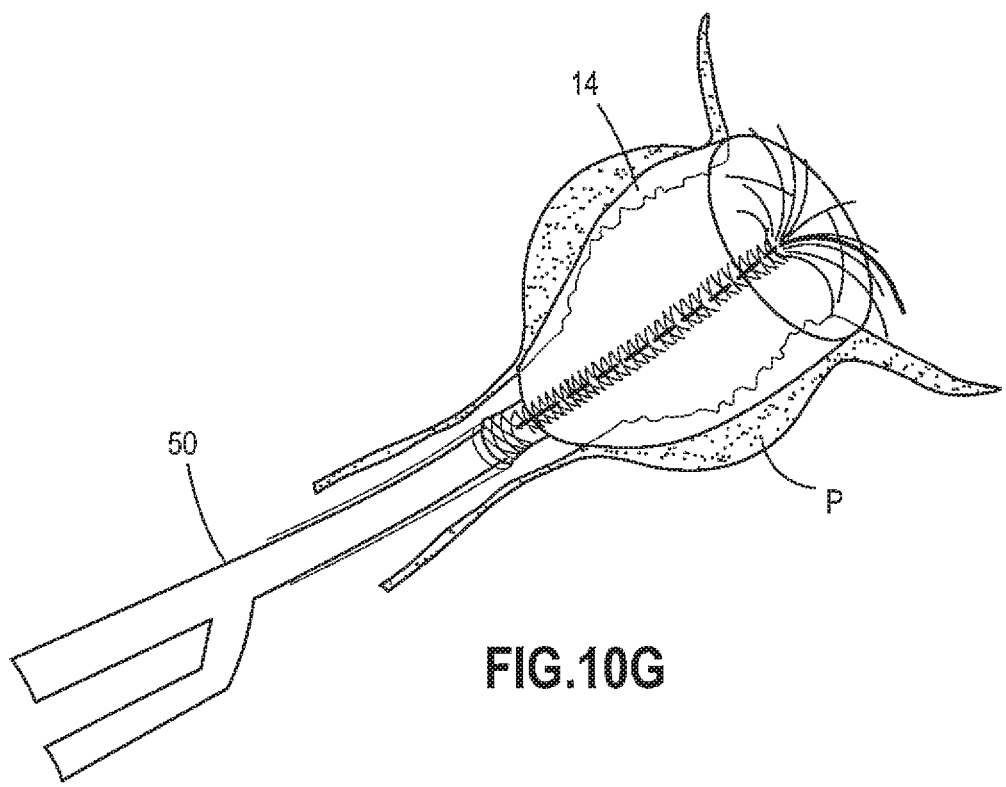
Figure 10H:
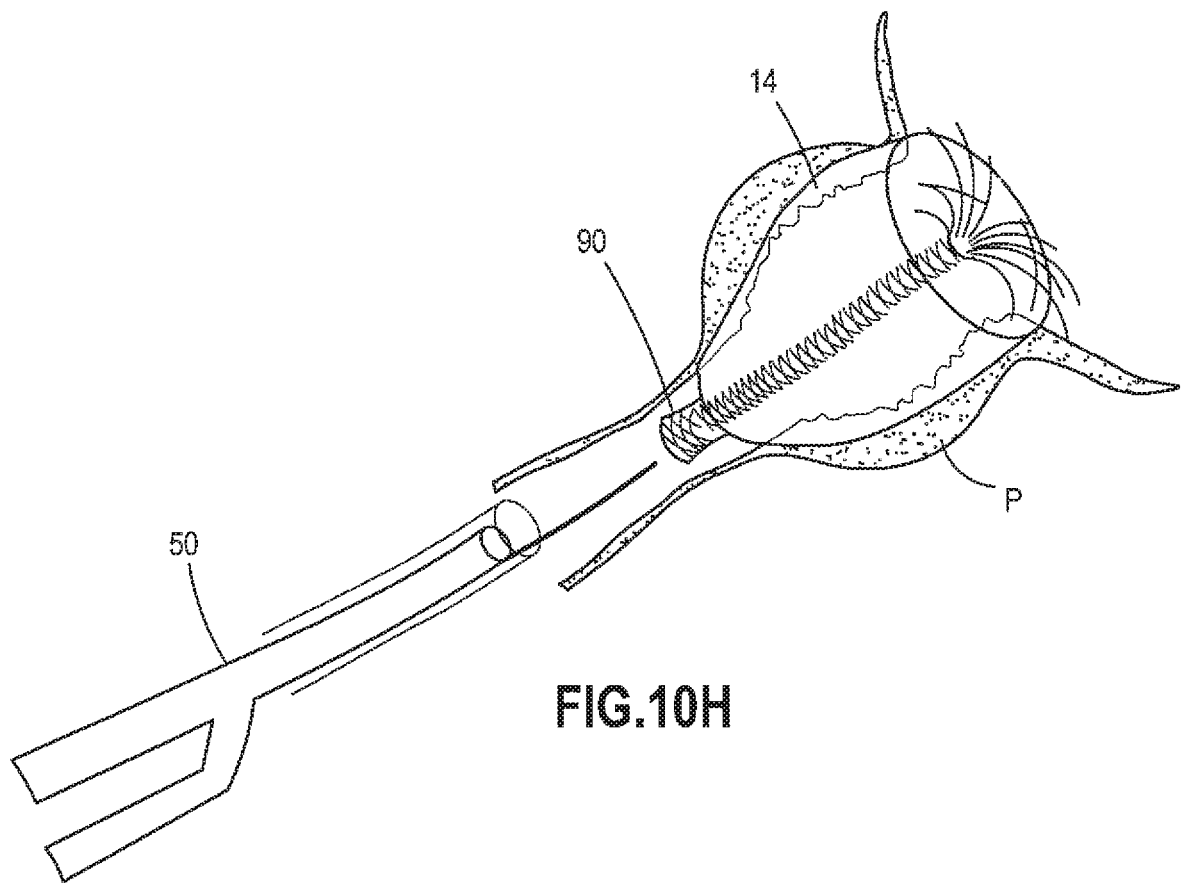

Referring now to FIGS. 10A-10H, the steps of one example method of using the prostatic chitosan stent 10 are shown. As shown in FIG. 10A, the stent 10 with the multi-lumen applicator 50 may be inserted into the urethra of a patient and into the prostate P. As can be seen, the stent 10 and the applicator 50 are serially arranged with the sheath 72 over the stent 10 such that the third layer 84 covers the second member 14 as well as the extended portion of the first member 12. As shown in FIG. 10B, the third layer 84 of the sheath 72 is removed such that the distal end of the first member 12 can be opened. As shown, the lattice or grille structure at the extended portion of the first member 12 is splayed. The second layer 82 remains on the second member 14. As shown in FIG. 10C, the balloon 60 is expanded, for example, via the injection of sterile water or by being inflated with a gas such as air or any inert gas. This expansion of the balloon 60 also expands the extended portion of the first member 12 to form the funnel. As shown in FIG. 10D, upon removal of the second layer 82 of the sheath 72, the second member 14 absorbs urine, and the chitosan material begins to expand. As shown in FIG. 10E, the second member 14 is expanded, and the stent 10 is maintained in place for a period of time (for example, three minutes) to allow for the full expansion of the second member 14. As shown in FIG. 10F, the balloon 60 is deflated, for example, by the suction of the sterile water from the balloon 60. As shown in FIG. 10G, the balloon 60 is extracted. Irrigation fluid may be provided through the second lumen of the multi-lumen tube. Drainage of the irrigation fluid (as well as other fluid from the bladder) may be through the first lumen. In general, the patient may be maintained catheterized in a recovery room. As shown in FIG. 10H the multi-lumen tube defining the applicator 50 is separated from the stent 10 and retracted. Retraction of the applicator 50 will generally be conditioned on an analysis of the drained urine and/or solution. The first layer 80 of the sheath 72 may be removed to allow the proximal end of the first member 12 to expand into the funnel shape, shown at 90. If the applicator 50 is retracted, the patient may be allowed to leave the place of treatment without any tubes and with only the bioresorbable stent 10 in the urethra.

In any example described herein, the first member 12 is comprised of at least one bioresorbable material such as, for example, poly(L-lactide) or poly(D,L-lactide), and the second member 14 is comprised of chistosan, which is used to support the healing of treated mucosa. Chitosan is a linear polysaccharide composed of randomly distributed $\beta$-(1→4)-linked D-glucosamine (deacetylated unit) and N-acetyl-D-glucosamine (acetylated unit).

Below are provided further descriptions of various non-limiting, exemplary embodiments. The below-described exemplary embodiments may be practiced in conjunction with one or more other aspects or exemplary embodiments. That is, the exemplary embodiments of the invention, such as those described below, may be implemented, practiced, or utilized in any combination (for example, any combination that is suitable, practicable, and/or feasible) and are not limited only to those combinations described herein and/or included in the appended claims.

In one exemplary embodiment, an apparatus comprises: a first layer, wherein the first layer comprises a scaffold structure forming an inner lumen along a length of the scaffold structure, and wherein the first layer comprises a bioresorbable material; a second layer on the first layer, wherein the second layer comprises a bioresorbable material configured to expand, wherein the second layer is positioned on the first layer such that ends of the first layer extend beyond ends of the second layer; and an expandable balloon located within a distal end of the inner lumen of the first layer.

The balloon may be expandable through the inner lumen, collapsible through the inner lumen, and retractable from a distal end of the first layer through the inner lumen. The apparatus may further comprise an applicator serially coupled to a proximal end of the apparatus, the applicator comprising a multi-lumen tube having at least an irrigation lumen through which a fluid may be delivered to a patient and a drain lumen through which the fluid may be removed from the patient. The applicator may be serially coupled to the proximal end of the apparatus using a compression covering on a distal end of the applicator and the proximal end of the apparatus. The compression covering may comprise a sheath having a first sheath layer coupling the distal end of the applicator to the proximal end of the applicator. The sheath may further comprise a second sheath layer on the first sheath layer and covering from a distal end of the second layer to the proximal end of the applicator such that upon removal of the second sheath layer the second layer may be exposed to a liquid. The sheath may further comprise a third sheath layer on the second sheath layer and covering from a distal end of the first layer to the proximal end of the applicator. At least one of a distal end of the first layer or a proximal end of the first layer may be configured to expand into a funnel shape. The bioresorbable material of the second layer may be chitosan.

In another exemplary embodiment, an apparatus comprises: a scaffold structure forming an inner lumen along a length thereof, the scaffold structure being substantially tubular in shape and expandable in radial directions from an axis extending longitudinally through the tubular shape of the scaffold structure, an expandable layer on the scaffold structure and covering a portion of the scaffold structure along a length thereof such that a distal end of the scaffold structure extends beyond a distal end of the expandable layer and a proximal end of the scaffold structure extends beyond a proximal end of the expandable layer, wherein a material of the second layer is configured to expand, and an expandable balloon located within the distal end of the scaffold structure.

The balloon may be accessible through the inner lumen. The balloon may be expandable through the inner lumen by injection of a liquid or a gas. The balloon may be expandable through the inner lumen and collapsible and retractable through the inner lumen. The apparatus may further comprise an applicator comprising a multi-lumen tube having at least an irrigation lumen through which a fluid may be delivered through the apparatus and to a patient and a drain lumen through which the fluid may be removed through the apparatus and from the patient, and a compression covering serially coupling the multi-lumen tube to the proximal end of the apparatus. The compression covering may comprise a first sheath layer coupling a proximal end of the scaffold structure to the applicator, a second sheath layer covering the expandable layer, and a third sheath layer covering from the distal end of the scaffold structure to the multi-lumen tube. A material of the scaffold structure and the material of the expandable layer may each comprise a bioresorbable material. The bioresorbable material of at least the expandable layer may comprise chitosan.

In another exemplary embodiment, a method comprises: inserting an apparatus into a prostatic urethra of a patient, wherein the apparatus comprises a stent comprising a first layer comprising a scaffold structure of a bioresorbable material forming an inner lumen along a length of the scaffold structure, a second layer on the first layer, the second layer comprising a bioresorbable material configured to expand and being positioned on the first layer such that ends of the first layer extend beyond ends of the second layer, and an expandable balloon located within a distal end of the inner lumen of the first layer; expanding the balloon to position the stent in the prostatic urethra; expanding the second layer to cause the second member to press against an inner surface of the prostatic urethra; and collapsing the balloon and retracting the balloon through the inner lumen.

Expanding the balloon may comprise injecting the balloon with a liquid or a gas. Expanding the second layer may comprise exposing the second layer to a liquid draining through the prostatic urethra. The method may further comprise serially coupling an applicator to a proximal end of the stent. Exposing the second layer to the liquid draining through the prostatic urethra may comprise removing a sheath layer at least partially serially coupling the applicator to the proximal end of the stent.

It should be understood that the foregoing description is only illustrative of the invention. Various alternatives and modifications can be devised by those skilled in the art without departing from the invention. Accordingly, the invention is intended to embrace all such alternatives, modifications, and variances which fall within the scope of the appended claims.

What is claimed is:

1. A stent apparatus for insertion into a prostatic urethra of a patient, comprising:
   a first layer, wherein the first layer comprises a scaffold structure forming an inner lumen along a length of the scaffold structure, and wherein the first layer comprises a bioresorbable material;
   a second layer on the first layer, wherein the second layer comprises a bioresorbable material configured to expand, wherein the second layer is positioned on the first layer such that ends of the first layer extend beyond ends of the second layer; and
   an expandable balloon located within a distal end of the inner lumen of the first layer, the balloon configured to expand such that at least a portion of the balloon extends distally beyond the distal end of the inner lumen of the first layer for engagement with surrounding tissue;
   wherein the second layer is configured to expand and press against an inner surface of the prostatic urethra when the second layer is exposed to a liquid draining through the prostatic urethra.

2. The apparatus of claim 1, wherein the balloon is expandable through the inner lumen, collapsible through the inner lumen, and retractable from a distal end of the first layer through the inner lumen.

3. The apparatus of claim 1, further comprising an applicator serially coupled to a proximal end of the apparatus, the applicator comprising a multi-lumen tube having at least an irrigation lumen through which a fluid may be delivered to a patient and a drain lumen through which the fluid may be removed from the patient.

4. The apparatus of claim 3, wherein the applicator is serially coupled to the proximal end of the apparatus using a compression covering on a distal end of the applicator and the proximal end of the apparatus.

5. The apparatus of claim 4, wherein the compression covering comprises a sheath having a first sheath layer coupling the distal end of the applicator to the proximal end of the applicator.

6. The apparatus of claim 5, wherein the sheath further comprises a second sheath layer on the first sheath layer and covering from a distal end of the second layer to the proximal end of the applicator such that upon removal of the second sheath layer the second layer may be exposed to a liquid.

7. The apparatus of claim 6, wherein the sheath further comprises a third sheath layer on the second sheath layer and covering from a distal end of the first layer to the proximal end of the applicator.

8. The apparatus of claim 1, wherein at least one of a distal end of the first layer or a proximal end of the first layer is configured to expand into a funnel shape.

9. The apparatus of claim 1, wherein the bioresorbable material of the second layer is chitosan.

10. A stent apparatus for insertion into a prostatic urethra of a patient, comprising:
    a scaffold structure forming an inner lumen along a length thereof, the scaffold structure being substantially tubular in shape and expandable in radial directions from an axis extending longitudinally through the tubular shape of the scaffold structure,
    an expandable layer on the scaffold structure and covering a portion of the scaffold structure along a length thereof such that a distal end of the scaffold structure extends beyond a distal end of the expandable layer and a proximal end of the scaffold structure extends beyond a proximal end of the expandable layer, wherein a material of the second layer is configured to expand, and
    an expandable balloon located within the distal end of the scaffold structure, the balloon configured to expand such that at least a portion of the balloon extends distally beyond the distal end of the scaffold structure for engagement with surrounding tissue, wherein the expandable layer is configured to expand and press against an inner surface of the prostatic urethra when the expandable layer is exposed to a liquid draining through the prostatic urethra.

11. The apparatus of claim 10, wherein the balloon is accessible through the inner lumen.

12. The apparatus of claim 11, wherein the balloon is expandable through the inner lumen by injection of a liquid or a gas.

13. The apparatus of claim 11, wherein the balloon is expandable through the inner lumen and collapsible and retractable through the inner lumen.

14. The apparatus of claim 10, further comprising an applicator comprising,
   a multi-lumen tube having at least an irrigation lumen through which a fluid may be delivered through the apparatus and to a patient and a drain lumen through which the fluid may be removed through the apparatus and from the patient, and
   a compression covering serially coupling the multi-lumen tube to the proximal end of the apparatus.

15. The apparatus of claim 14, wherein the compression covering comprises a first sheath layer coupling a proximal end of the scaffold structure to the applicator, a second sheath layer covering the expandable layer, and a third sheath layer covering from the distal end of the scaffold structure to the multi-lumen tube.

16. The apparatus of claim 10, wherein a material of the scaffold structure and the material of the expandable layer each comprises a bioresorbable material.

17. The apparatus of claim 16, wherein the bioresorbable material of at least the expandable layer comprises chitosan.

18. A method, comprising:
   inserting an apparatus into a prostatic urethra of a patient, wherein the apparatus comprises a stent comprising a first layer comprising a scaffold structure of a bioresorbable material forming an inner lumen along a length of the scaffold structure, a second layer on the first layer, the second layer comprising a bioresorbable material configured to expand and being positioned on the first layer such that ends of the first layer extend beyond ends of the second layer, and an expandable balloon located within a distal end of the inner lumen of the first layer;
   expanding the balloon to position the stent in the prostatic urethra;
   expanding the second layer to cause the second layer to press against an inner surface of the prostatic urethra, wherein expanding the second layer comprises exposing the second layer to a liquid draining through the prostatic urethra; and
   collapsing the balloon and retracting the balloon through the inner lumen.

19. The method of claim 18, wherein expanding the balloon comprises injecting the balloon with a liquid or a gas.

20. The method of claim 18, further comprising serially coupling an applicator to a proximal end of the stent.

21. The method of claim 20, wherein exposing the second layer to the liquid draining through the prostatic urethra comprises removing a sheath layer at least partially serially coupling the applicator to the proximal end of the stent.

* * * * *